(12) United States Patent
Shah et al.

(10) Patent No.: US 9,976,963 B2
(45) Date of Patent: May 22, 2018

(54) MICROCUVETTE CARTRIDGE

(71) Applicant: Integrated Plasmonics Corporation, San Francisco, CA (US)

(72) Inventors: Nilesh Dinbandhu Shah, San Francisco, CA (US); Albert Jerwen Mach, San Jose, CA (US)

(73) Assignee: INTEGRATED PLASMONICS CORPORATION, San Francisco, CA (US)

( * ) Notice: Subject to any disclaimer, the term of this patent is extended or adjusted under 35 U.S.C. 154(b) by 404 days.

(21) Appl. No.: 14/095,971

(22) Filed: Dec. 3, 2013

(65) Prior Publication Data

US 2014/0176939 A1 Jun. 26, 2014

Related U.S. Application Data

(60) Provisional application No. 61/745,503, filed on Dec. 21, 2012, provisional application No. 61/778,315, filed on Mar. 12, 2013.

(51) Int. Cl.
*G01N 21/84* (2006.01)
*B01L 3/00* (2006.01)

(52) U.S. Cl.
CPC ...... *G01N 21/8483* (2013.01); *B01L 3/50273* (2013.01); *B01L 3/502715* (2013.01);
(Continued)

(58) Field of Classification Search
CPC .......... G01N 21/8483; B01L 3/502715; B01L 3/50273
See application file for complete search history.

(56) References Cited

U.S. PATENT DOCUMENTS 4,516,857 A 5/1985 Preston et al.
4,659,222 A 4/1987 Ekholm
(Continued)

FOREIGN PATENT DOCUMENTS

EP 1 217 426 A1 6/2002
WO 1998/034098 A1 8/1998
(Continued)

OTHER PUBLICATIONS

International Search Report (ISR) issued in PCT/US2013/072927 dated Apr. 2014.
(Continued)

*Primary Examiner* — Tri Ton
*Assistant Examiner* — Rebecca C Bryant
(74) *Attorney, Agent, or Firm* — Chen Yoshimura LLP

(57) ABSTRACT

A microcuvette cartridge for optical measurement of a specimen includes: a substrate having a recess on an upper surface thereof to receive a fluid specimen therein, the substrate having a plurality of cavities therein to receive the fluid specimen transported from the recess, the substrate further defining a plurality of channels communicating with the recess and with the plurality of cavities, respectively, to transport the fluid specimen from the recess to the plurality of cavities, said substrate further having one or more of windows at positions corresponding to the plurality of cavities, the windows being transparent to wavelength of light with which the optical measurement is to be carried out so as to allow the light to interact with the fluid specimen in the cavities; and a transport mechanism to promote and complete flows of the fluid specimen from the recess to the plurality of cavities through the plurality of channels.

7 Claims, 16 Drawing Sheets

(52) U.S. Cl.
CPC ... *B01L 2200/027* (2013.01); *B01L 2300/043* (2013.01); *B01L 2300/069* (2013.01); *B01L 2300/0645* (2013.01); *B01L 2300/0654* (2013.01); *B01L 2300/0681* (2013.01); *B01L 2300/0816* (2013.01); *B01L 2300/0825* (2013.01); *B01L 2300/0864* (2013.01); *B01L 2300/0883* (2013.01); *B01L 2300/1827* (2013.01); *B01L 2400/0406* (2013.01); *B01L 2400/049* (2013.01); *B01L 2400/0481* (2013.01)

(56) References Cited

U.S. PATENT DOCUMENTS

| | | | |
|---|---|---|---|
| 5,116,759 A | | 5/1992 | Klainer et al. |
| 5,356,010 A | * | 10/1994 | Weinstein ............... B65D 5/42 206/528 |
| 5,644,512 A | | 7/1997 | Chernoff et al. |
| 5,674,457 A | | 10/1997 | Williamsson et al. |
| D433,150 S | | 10/2000 | Wahlqvist et al. |
| 6,425,888 B1 | * | 7/2002 | Embleton ............. A61F 9/0008 604/290 |
| 6,838,650 B1 | | 1/2005 | Toh |
| 7,104,417 B2 | * | 9/2006 | Hilliard ............. B65D 83/0454 221/25 |
| 7,175,044 B2 | * | 2/2007 | Benktzon ........... B65D 83/0463 206/531 |
| 7,466,409 B2 | | 12/2008 | Scherer et al. |
| 8,076,128 B2 | | 12/2011 | Liederman et al. |
| 8,231,268 B2 | | 7/2012 | Krol et al. |
| 8,284,401 B2 | | 10/2012 | Choi et al. |
| 2005/0106066 A1 | * | 5/2005 | Saltsman ............. B01F 5/0473 422/504 |
| 2005/0114332 A1 | | 5/2005 | Lee et al. |
| 2006/0034729 A1 | | 2/2006 | Poponin |
| 2007/0070347 A1 | | 3/2007 | Scherer et al. |
| 2008/0135739 A1 | | 6/2008 | Kim et al. |
| 2009/0075390 A1 | * | 3/2009 | Linder .................. A61L 2/0082 436/161 |
| 2010/0039648 A1 | | 2/2010 | Garcia da Fonseca |
| 2010/0046060 A1 | | 2/2010 | Lee et al. |
| 2010/0143963 A1 | * | 6/2010 | Pollack ............. B01L 3/502792 435/29 |
| 2010/0157306 A1 | | 6/2010 | Choi et al. |
| 2011/0041591 A1 | * | 2/2011 | Gupta .................. B01L 3/5023 73/64.56 |
| 2011/0085167 A1 | | 4/2011 | Guan et al. |
| 2011/0111487 A1 | | 5/2011 | Goh et al. |
| 2012/0225475 A1 | | 9/2012 | Wagner et al. |

FOREIGN PATENT DOCUMENTS

| | | |
|---|---|---|
| WO | 2006/009724 A2 | 1/2006 |
| WO | 2011/106057 A2 | 9/2011 |
| WO | 2012/054351 A2 | 4/2012 |
| WO | 2014/089120 A1 | 6/2014 |
| WO | 2014/123613 A1 | 8/2014 |
| WO | 2014/143234 A1 | 9/2014 |
| WO | 2014/143235 A1 | 9/2014 |
| WO | 2014/158248 A1 | 10/2014 |

OTHER PUBLICATIONS

Written Opinion (PCT/ISA/237) issued in PCT/US2013/072927 dated Apr. 2014.
Huang et al., "Micro-hole drilling with femtosecond fiber laser", SPIE Paper No. 8607-19, Photonics West 2013, Feb. 2-7, 2013.
International Search Report (ISR) issued in PCT/US2013/072929 dated Apr. 2014.
Written Opinion (PCT/ISA/237) issued in PCT/US2013/072929 dated Apr. 2014.
International Search Report (ISR) issued in PCT/US2013/072930 dated Apr. 2014.
Written Opinion (PCT/ISA/237) issued in PCT/US2013/072930 dated Apr. 2014.
International Search Report (ISR) issued in PCT/US2013/072932 dated Apr. 2014.
Written Opinion (PCT/ISA/237) issued in PCT/US2013/072932 dated Apr. 2014.
International Search Report (ISR) issued in PCT/US2013/072936 dated Apr. 2014.
Written Opinion (PCT/ISA/237) issued in PCT/US2013/072936 dated Apr. 2014.
Fledler, "Incoherent Broad-Band Cavity-Enhanced Absorption Spectroscopy", 2005, Berlin.
Barron, "Basics of UV-Visible Spectroscopy", Physical Methods in Chemistry and Nano Science, Jun. 5, 2010.
Chen et al., "A CMOS Image Sensor Integrated with Plasmonic Colour Filters", Plasmonics, Dec. 2012, vol. 7, Issue 4, (abstract) Springer Link.
Mansuripur et al., "Plasmonic nano-structures for optical data storage", Optics Express, Aug. 3, 2009, vol. 17, No. 16, pages 14001-14014.
Genet et al., "Light in tiny holes", nature, Jan. 4, 2007, vol. 445, pp. 39-46.
Koerkamp et al., "Strong Influence of Hole Shape on Extraordinary Transmission through Periodic Arrays of Subwavelength Holes", Physical Review Letters, May 7, 2004, vol. 92, No. 18, pp. 183901-1-183901-4.
Jones et al., "Surface Plasmon assisted extraordinary transmission in metallic nanohole arrays and its suitability as a bio-sensor", Journal of Physics: Conference Series 307, IOP Publishing, 2011, pp. 1-7.
Tok et al., "Unidirectional broadband radiation of honeycomb plasmonic antenna array with broken symmetry", Optics Express, Nov. 7, 2011, vol. 19, No. 23, pp. 22731-22742.
Pacifici et al., "Universal optical transmission features in periodic and quasiperiodic hole arrays", Optics Express, Jun. 9, 2008, vol. 16, No. 12, pp. 9222-9238.
Singh et al., "Surface Plasmon Resonance Enhanced Transmission of Light through Gold-Coated Diffraction Gratings", Analytical Chemistry, May 15, 2008, vol. 80, No. 10, pp. 3803-3810.

* cited by examiner

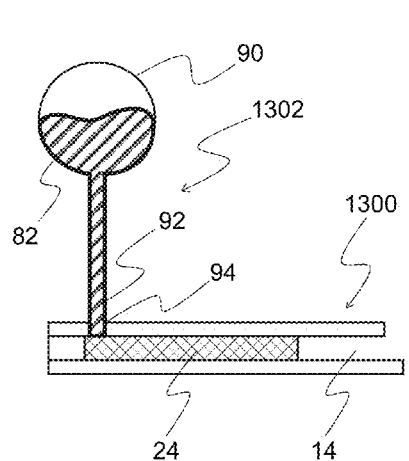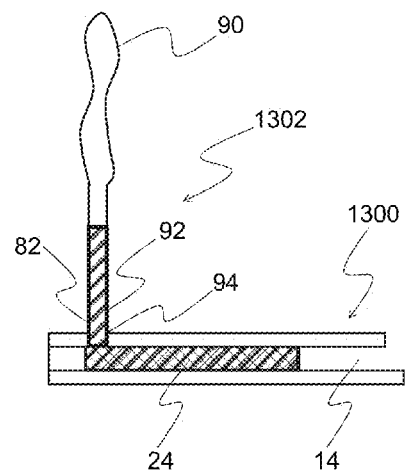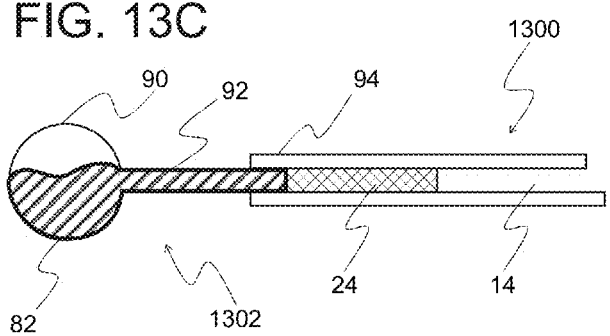

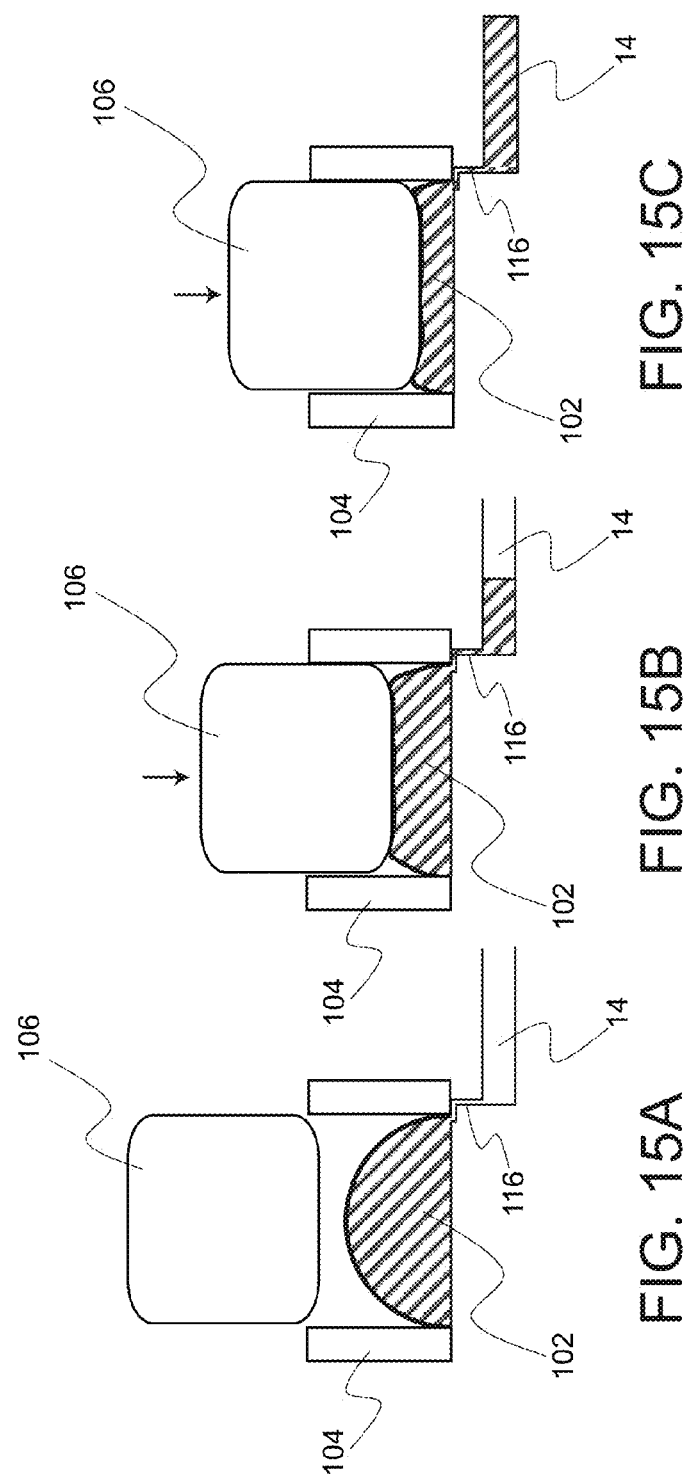

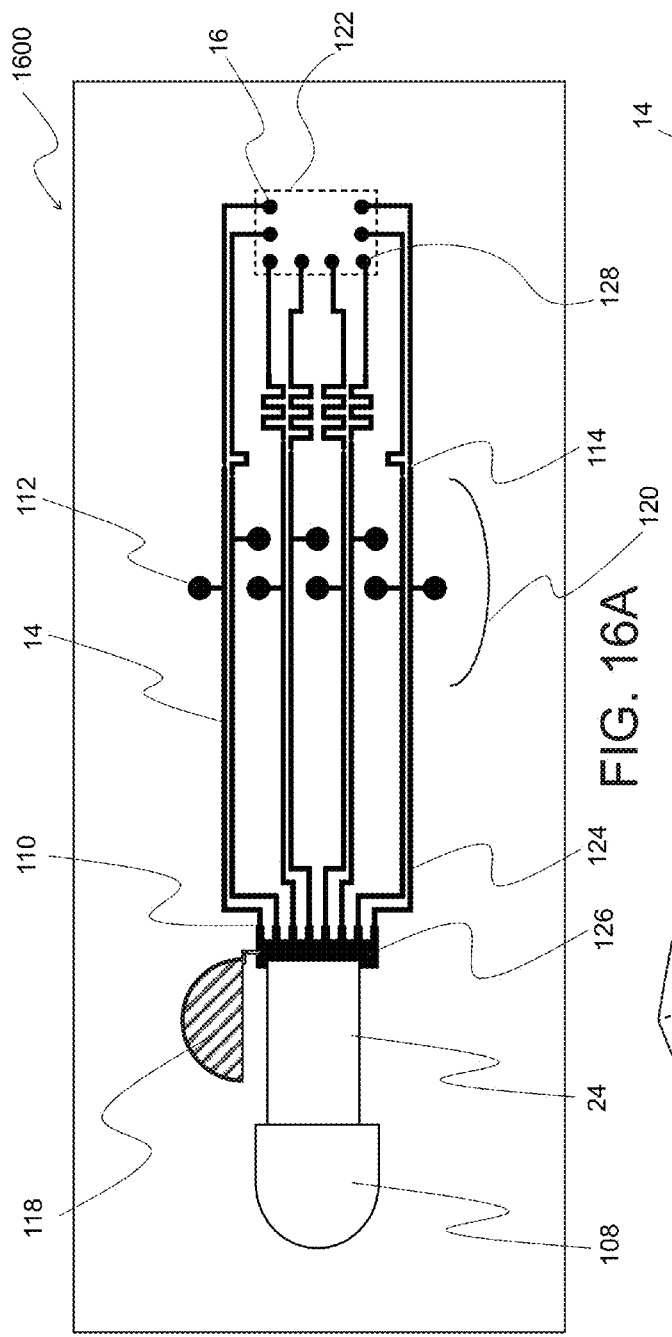
FIG. 16A
FIG. 16C
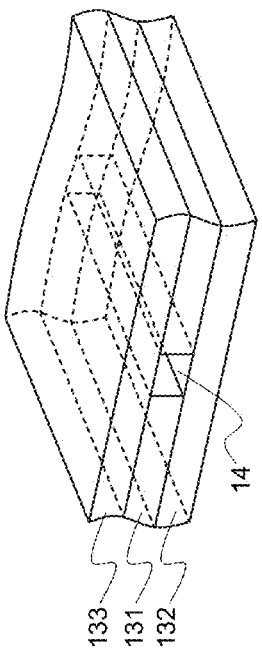
FIG. 16B

MICROCUVETTE CARTRIDGE

FIELD OF THE INVENTION

This invention relates to a microcuvette cartridge for use in optical analysis of a specimen held by the cartridge.

BRIEF SUMMARY OF THE INVENTION

The present invention is directed to a small, portable microcuvette cartridge.

An object of the present invention is to provide an improved small-sized microcuvette cartridge that has multiple microcuvettes integrated therein suited for optical analysis, thereby providing increased ease of use and improved portability to the users and lab technicians.

Another object of the present invention is to ensure reliability in filling the specimen into the respective cuvettes in such a microcuvette cartridge.

Another object of the present invention is to provide a single portable microcuvette cartridge having multiple microcuvettes suited for clinically relevant blood test panels including one or more tests comprising the Comprehensive Metabolic Panel (CMP) or like panels.

To achieve these and other advantages and in accordance with the purpose of the present invention, as embodied and broadly described, in one aspect, the present invention provides a microcuvette cartridge for optical measurement of a specimen including: a substrate having a recess on an upper surface thereof to receive a fluid specimen therein, said substrate having a plurality of cavities therein to receive the fluid specimen transported from the recess, said substrate further defining a plurality of channels communicating with the recess and with the plurality of cavities, respectively, to transport the fluid specimen from the recess to the plurality of cavities, respectively, said substrate further having one or more of windows at positions corresponding to the plurality of cavities, the windows being transparent to wavelength of light with which the optical measurement is to be carried out so as to allow the light to interact with the fluid specimen in the cavities, and a transport mechanism to promote and complete flows of the fluid specimen from the recess to the plurality of cavities through the plurality of channels.

In another aspect, the present invention provides a microcuvette cartridge for optical measurement of a specimen, including a substrate having a recess on an upper surface thereof to receive a fluid specimen therein, the substrate having a plurality of cavities therein to receive the fluid specimen transported from the recess, the substrate further defining a plurality of channels communicating with the recess and with the plurality of cavities, respectively, to transport the fluid specimen from the recess to the plurality of cavities, the substrate further having one or more of windows at positions corresponding to the plurality of cavities, the windows being transparent to wavelength of light with which the optical measurement is to be carried out so as to allow the light to interact with the fluid specimen in the cavities, wherein at least a portion of each of the plurality of channels is made of a shrinkable porous material so as to remove a gas from the channels, and wherein at least some of the plurality of channels have at least one flow restrictor to temporarily stop a flow of the fluid specimen in the channel.

Additional features and advantages of the invention will be set forth in the description which follows and in part will be apparent from the description, or may be learned by practice of the embodiments of the invention disclosed herein. The other objectives and advantages of the invention will be realized and attained by the structure particularly pointed out in the written description and claims hereof and/or in the appended drawings.

It is to be understood that both the foregoing general description and the following detailed description are exemplary and explanatory, and are intended to provide further explanation of the invention as claimed in a patent(s) originating from this application.

BRIEF DESCRIPTION OF THE SEVERAL VIEWS OF THE DRAWINGS

FIGS. 13A to 13C illustrate a fluid transport scheme of a microcuvette cartridge with a blood dropper according to an embodiment of the present invention.

FIGS. 15A to 15C illustrate a multistep fluid transport scheme of a microcuvette cartridge with a blister pack according to an embodiment of the present invention.

FIGS. 16A to 16C shows a microcuvette cartridge according to an embodiment of the present invention.

DETAILED DESCRIPTION OF THE INVENTION

Figure 1:
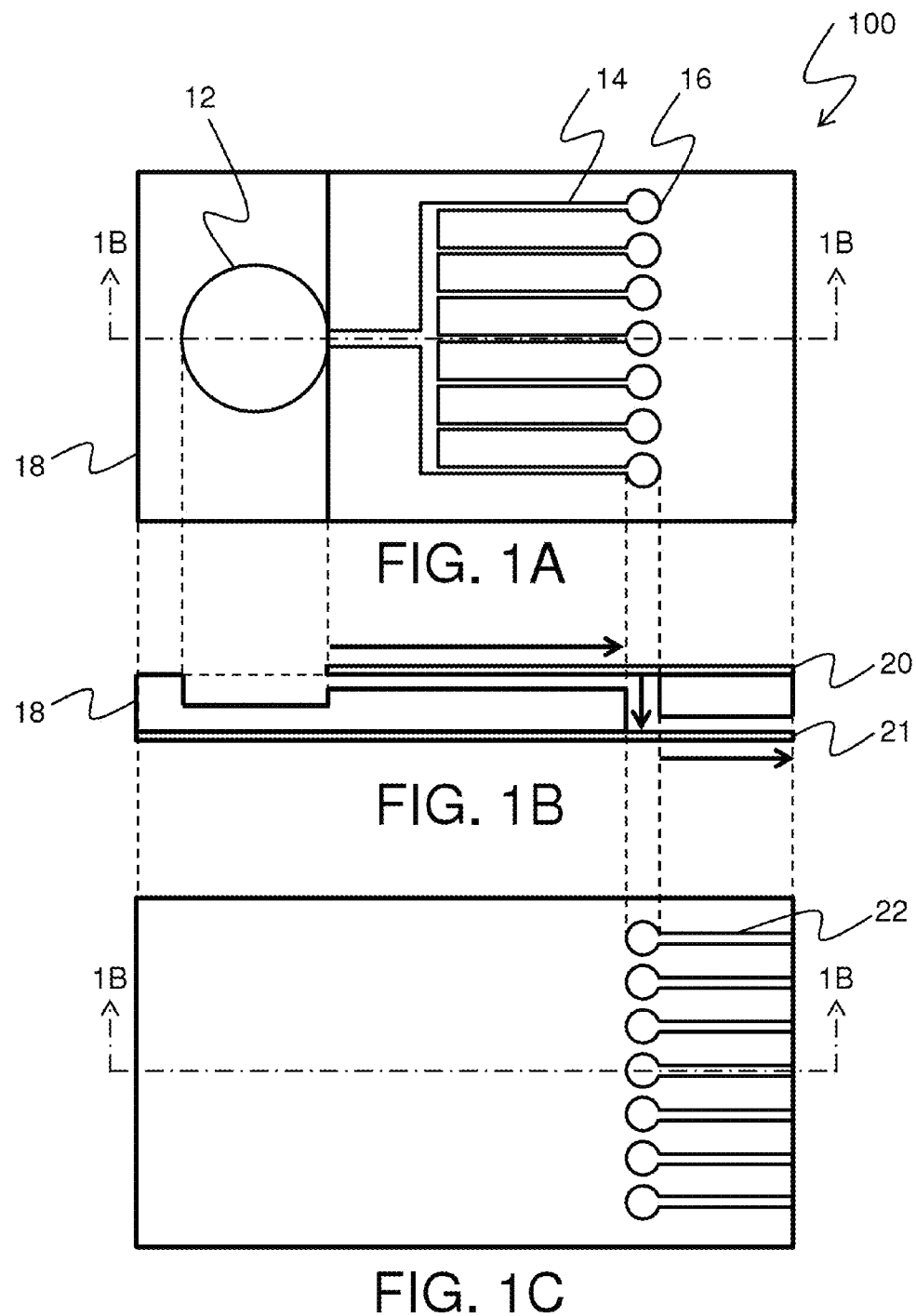
FIG. 1A is a top view of a microcuvette cartridge according to an embodiment of the present invention.
FIG. 1B is a cross section of a microcuvette cartridge according to the embodiment of the present invention.
FIG. 1C is a bottom view of a microcuvette cartridge according to an embodiment of the present invention.

FIG. 1A is a top view of the microcuvette cartridge 100 according to an embodiment of the present invention. By using this microcuvette cartridge 100, a fluid containing a target analyte can be placed in a plurality of microcuvettes strategically arranged in the cartridge 100. The microcuvette cartridge 100 has a recess 12 (also referred to as chamber), channels 14, and microcuvettes (cavities) 16. When fluid is introduced into the recess 12, the fluid is carried from the recess 12 to each microcuvette 16 through the channels 14. FIG. 1B is a cross section of the microcuvette cartridge 100. The chamber 12 has a certain depth in the intermediate substrate 18 and can receive and hold fluid. The grooves having a certain design depth are formed on the upper surface of intermediate substrate 18, and when coupled with a upper plate 20 (described below), they define respective channels 14 to provide for passages for the fluid to pass through. The depth of the chamber 12 and the dimensions of the channel 14 are appropriately designed. For example, the depth of the channel 14 may be greater than the depth of the chamber 12. Each of the microcuvettes 16 comprises a cavity structure so that the microcuvettes 16 can be filled with the fluid. Above and below the intermediate substrate 18, the upper plate 20 and a lower plate 21 are provided. The upper plate 20 and/or the lower plate 21 should be transparent for the wavelengths of light that interacts with the specimen in the microcuvette at positions corresponding to the microcuvettes 16 so that optical examination can be conducted. Some portions of the upper plate 20 and the lower plate 21 may be configured to be gas-permeable and not liquid-permeable or to be hydrophobic and porous so that excess gas or air may escape and promote smooth flow of the fluid through the channels 14.

The microcuvettes cartridge 100 of this embodiment is designed to be portable and much smaller than conventional microcuvettes to provide for ease of use and convenience to the users. Preferred dimensions of the cartridge are in the order of a few to several centimeters in width and length and a few millimeters in thickness. Thus, each of the microcuvettes 16 may be as small as a few millimeters or submillimeters in diameter, for example. The dimensions of the channels 14 may be as small as a few hundred microns or may be as large as the diameter of microcuvette 16 in width and height in some embodiments. For example, the diameter of each cuvettes can be 50-400 μm and the height can be 100 μm-3 mm. In one example, a single cartridge can have as many as 50 microcuvettes, depending on the overall dimensions of the cartridge and required dimensions for the microcuvettes. Furthermore, a region of the cartridge where microcuvettes 16 will be optically coupled to an external spectrophotometer instrument for optical imaging and/or absorbance measurements may be constructed of materials different from the remainder of the cartridge to enhance the optical clarity for better optical coupling with the specimen in the microcuvettes. Such a detection region may be one large reservoir with the size of a well in a 96-well-plate or many individual areas corresponding to respective microcuvettes. Moreover, the microcuvette can have various shapes and dimensions to enhance absorbance measurements from the spectrometer. The heights of the microcuvettes 16 can range from 100 μm to 3 mm, for example. The diameters or widths of the microcuvettes 16 can vary between 50 to 400 μm or smaller or larger, for example.

In this embodiment, the flow of the fluid received by the chamber 12 in the channels 14 is generated primarily by capillary action of the fluid within the channels 14. FIG. 1C is a bottom view of the microcuvette cartridge 100. The microcuvette cartridge 100 has back channels (discharge channels) 22 respectively connected to the plurality of microcuvettes to avoid unwanted pressure development inside the channels 14 when capillary forces causes the fluid to move through the channels 14. As the three arrows indicate in FIG. 1B, the fluid received at the chamber 12 goes through the channels 14, the microcuvette 16, and the back channels 22. The dimensions and surface conditions of the channels 14 and the back channels 22 as well as the material of the structures that defines the channels 14 and the back channels 22 are appropriately chosen to promote efficient flow of the fluid from the chamber 12 to the microcuvettes 16 and to allow the fluid to stay in the microcuvettes for a sufficient period of time for optical analysis. Since the two ends are open, capillary action occurs in all of the channels. The channels 14 may be made of a material which is hydrophilic, or be treated, for example plasma treated, to render the channels 14 hydrophilic, or may have a surface coating which renders the channels 14 hydrophilic, while the back channels 22 may be made of a material which is hydrophobic, or may be treated, for example plasma treated, to render the back channels 22 hydrophobic, or may have a surface coating which renders the back channels hydrophobic. Although FIG. 1A depicts the discharge channels 22 on the backside of the cartridge 100, the discharge channels may be disposed on the upper side. Other fluid passages are also possible.

The microcuvette cartridge 100 may be composed of a polymer or polymers, or glass or a hybrid thereof. The appropriate polymers include thermoset polyester (TPE), polyurethane methacrylate (PUMA), Norland Optical Adhesive (NOA), polystyrene (PS), polycarbonate (PC), polyvinyl chloride (PVC), cyclic olefin copolymer (COC), polymethyl methacrylate (PMMA), polydimethylsiloxane (PDMS), polyether ether ketone (PEEK), high-density polyethylene (HDPE), Kel-F®, polysulfone, Tefzel®, Delrin®, SU-8, Polytetrafluoroethylene (PTFE), ZEONOR®, pressure sensitive adhesive (PSA) and any combinations or copolymerization thereof. The materials on the top and bottom of each of the microcuvettes 16 should be such that it can effectively transmit light with a wavelength of interest. Purified glass, quartz glass, soda lime, fused silica, Borofloat®, and other appropriate materials may be used depending on the wavelength or other properties of the light. Also, to avoid crosstalk between light rays that pass through adjacent microcuvettes, the material of the structure that defines the microcuvettes should be chosen appropriately depending on the dimensions and intervals, for example, of the multiple microcuvettes.

With regard to the manufacturing method of the microcuvette cartridge 100, the micro- and milli-structures, such as the chamber, the channels, and the microcuvette, described above as an example, may be made of polymer by molding, machining and/or laser cut together with appropriate lamination or heat bonding techniques. For this purpose, laser machining, mechanical drilling, powder blasting, waterjet cutting, injection molding, hot embossing, and/or polymer casting, etc., can be used. Other appropriate materials include silica, quartz, and silicon, where micro- and milli-structures are micromachined. As described above, the microcuvette cartridge can be made from separate layers, such as the upper plate, the intermediate substrate, and the lower plate, using said materials. For example, an intermediate substrate can be machined to have grooves engraved therein respectively corresponding to the chamber, the channels, and the microcuvettes. Thereafter, a top plate and a bottom plate can be attached to the substrate to define the channels. The surfaces of these polymer and glass materials that will be in contact with the fluid can be chemically treated and modified to enhance or decrease fluid transport, and to prevent nonspecific binding to the surface.

Additionally, in case that the cartridge is designed to receive blood as the fluid to be examined, the cartridge may include filter paper for plasma separation from blood, packaged liquid solutions for diluent and reagents, defined geometric regions allowing actuators to push on said liquid solutions, and patterned electrodes for a thermocouple.

Figure 2:
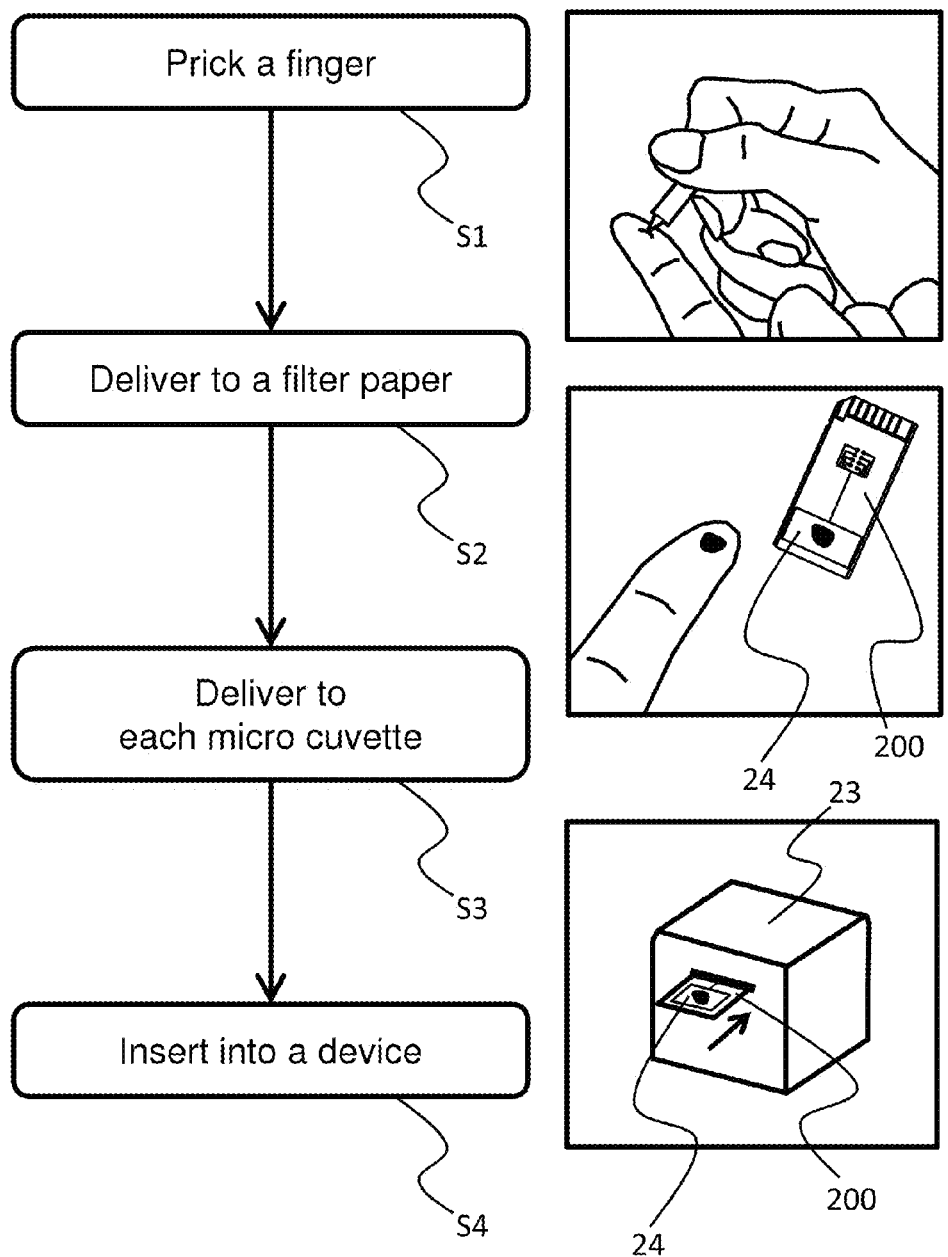
FIG. 2 is a flow chart for showing one usage of a microcuvette cartridge according to an embodiment of the present invention.

FIG. 2 is a flow chart for showing the usage of a microcuvette cartridge 200 according to an embodiment of the present invention. The microcuvette cartridge 200 in this embodiment has a form factor of the SD card specifications, and is equipped with a filter 24 for receiving and filtering blood. The detailed structure of preferred configurations of the microcuvette cartridge 200 will be described later.

As shown in FIG. 2, in step S1, a finger is pricked using a lancet. Then, in step S2, blood on the finger is delivered to a filter paper 24 on the cartridge 200. In step S3, the blood absorbed by the filter paper 24 is delivered to the each microcuvette by capillary force. At step S4, the cartridge 200 is inserted into an optical measurement device 23 and optical measurement/examination will be conducted. The order of step S3 and step S4 can be reversed such that flow actuation can occur during the insertion process.

Figure 3:
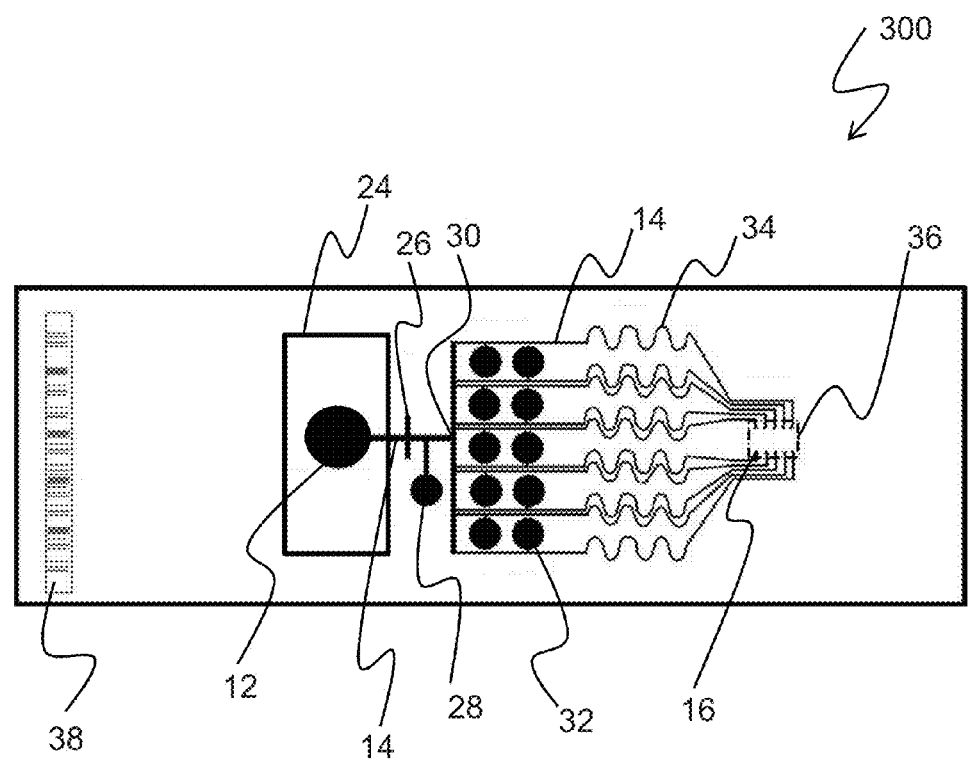
FIG. 3 is a schematic view of a microcuvette cartridge according to an embodiment of the present invention.

FIG. 3 shows another embodiment of the present invention. The microcuvette cartridge 300 according to the present embodiment can deliver a very small amount of pinprick blood (for example 5-30 μL) to a plurality of strategically placed microcuvettes 16. The microcuvette cartridge 300 has a chamber 12, a filter paper 24, a membrane 26, a first blister pack 28, a metering point 30, a plurality of second blister packs 32, channels 14, mixing channels 34, and microcuvettes 16. A detection region 36 is defined as a region where the array of the microcuvettes 16 is disposed. A barcode 38 is affixed to one end of the cartridge 300.

Each of the blister packs (or also referred to as "blister packages") 28, 32 may be in the form an enclosed cavity filled with liquid, dried reagents, or a combination of both products. In one example, the constituent components of the blister pack include a forming film, a coating on the film, a sealing agent, and a lid. The film contains the cavity that receives the liquid and/or dried product. The cavity can be in the shape of a hemisphere or hemiellipsoid and may include a channel protruding on one side to guide fluid in that direction when the contents of the blister pack is emptied. It can be constructed with a cold-formed aluminum or thermoformed plastic, which includes PVC, polypropyle (PP), polyester (PET), PVDC, CTFE, PP, and/or PS, for example. The coating may be a thin laminate that minimizes gas and moisture permeability and can be made from similar plastic materials. The lid can provide the base and seal that holds the contents in the forming film. It can be formed from clear plastic or combination of plastic, paper, and/or foil. The lid may be thin enough, with a thickness less than 0.7 mm, so that pressure applied to the forming film pushes the contents of the product through the lid and into a fluid channel underneath. The sealing agent provides a bond between the forming film and the lid through a heat-press process. The blister pack can be "activated" through a blunt actuator that mechanically pushes down on the apex of the hemisphere or hemiellipsoid or a needle placed in or near the fluid channel. The applied pressure can force fluid out of the blister pack into a region with the least fluidic resistance while the needle pokes a hole in the pack and releases the contents. For the liquid contents to escape the package, a layer underneath the blister pack may contain micro- and milli-fluidic channels to route fluids through the cartridge system. In this embodiment, the blister pack 28 is disposed on the main channel, and the blister packs 32 are disposed on the respective branched-off channels 14.

Blood is absorbed by the filter paper 24 such that only the target analytes can pass through the filter paper 24 and flow into the channel 14. For example, the filter paper 24 is configured to separate plasma from other elements such as cells and other blood proteins, trapping blood cells and extracellular debris, while plasma passes through the filter paper 24. Also, impurities contained in the blood can be removed using the filter paper 24. The filter paper 24 may be either hydrophilic or hydrophobic. After filtration, the fluid reaches membrane 26, which prevents backflow of the fluid. After passing through the membrane 26, the fluid may meet a first blister pack 28. The first blister pack 28 may hold a liquid solution such as a diluent or a reagent, and upon discharge, the liquid solution is mixed with fluid filtered by filter paper 24. In this embodiment, some or each of the blister packs 28, 32 have two primary functions: one is pushing the fluid and generating the flow, and the other one is providing the diluent or the reagent to the stream of the fluid. One blister pack may assume one of these functions or both. As the second function, for example, anticoagulant may be included in as the liquid solution to make it more difficult for blood to clot. Also, liquid stable reagents may also be included in as the liquid solution. At the metering point 30, the fluid is metered out by the channels 14. The first blister pack 28 may be used to push and to aliquot fluid evenly to individual channels 14. After passing the metering point 30, each channel 14 meets each second blister pack 32, which contains the same or different liquid solution. Each of the first and second blister packs can add certain designed amounts of the liquid solution to the stream of the fluid. In this embodiment, to mix the liquid solution and the fluid sufficiently, mixing channels 34 are provided. The mixing channels 34 may be serpentine channels as shown in the figure. After passing through the mixing channels 34, the fluid is transported to the microcuvettes 16 in the detection region 36. The analyte in each microcuvette 16, which may have reacted with a certain liquid solution can be analyzed by an optical measurement device. A barcode 38 may be used to relate the cartridge 300 to an individual.

The amount of fluid flowing in can be controlled by changing the section area of each channel 14. By varying the channel width and height, the dilution level of the fluid can be changed. The cartridge can transport a desired amount of the fluid to each microcuvette 16 for measurement/analysis with only the required amount of blood so that the total collection quantity of blood can be very small.

The liquid solution can be in the form of a liquid absorbed by paper or printed on paper. Also, the form of lyophilized beads or dissolvable film can be used. Lyophilized beads and dissolvable film can be put inside the microcuvettes in advance. The liquid solution may also be dried following deposition into the microcuvettes and flow channels.

Figure 4:
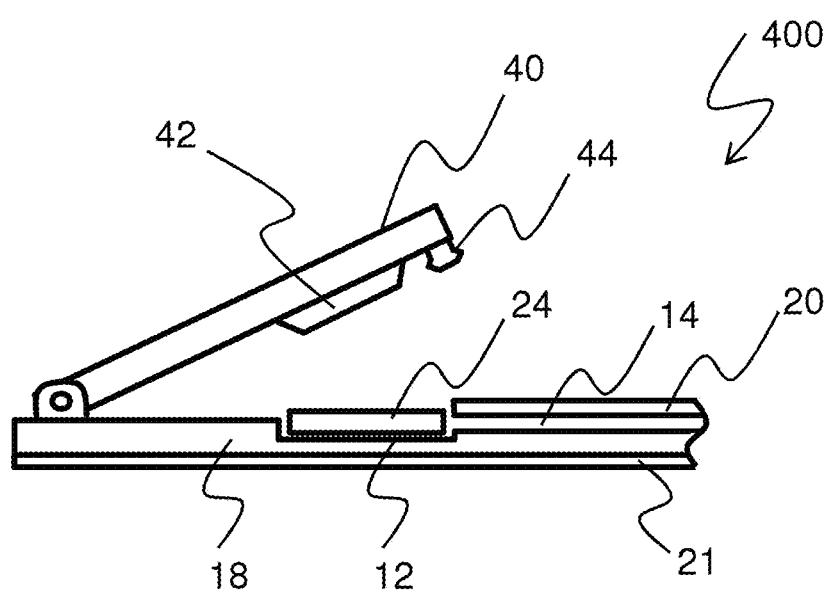
FIG. 4 is a cross section of a microcuvette cartridge with a lid according to an embodiment of the present invention.

FIG. 4 shows another embodiment of the present invention. FIG. 4 shows a cross section of a microcuvette cartridge 400, showing an example of the transport mechanism.

In this embodiment, a lid 40 is installed to generate flows in the respective channels. The lid 40 has a bump 42 and a snap 44. The filter paper 24 is positioned in the chamber 12 and the chamber 12 is connected to the channels 14. One end of the lid 40 is connected to an intermediate substrate 18 using a hinge and the other end of the lid 40 has the bump 42 and the snap 44. The bump 42 is positioned corresponding to the position of the chamber 12 so as to squeeze blood from the filter paper 24 and make it flow from the filter paper 24 to the channels 14. The snap 44 can be used to hold the bump 42 in the chamber 12 surely.

Alternatively, or in addition, the lid 40 may engage with blister packs 28 and/or 32 of FIG. 3 when closed so that they are collapsed to discharge the liquid solutions or reagents.

Figure 5A:
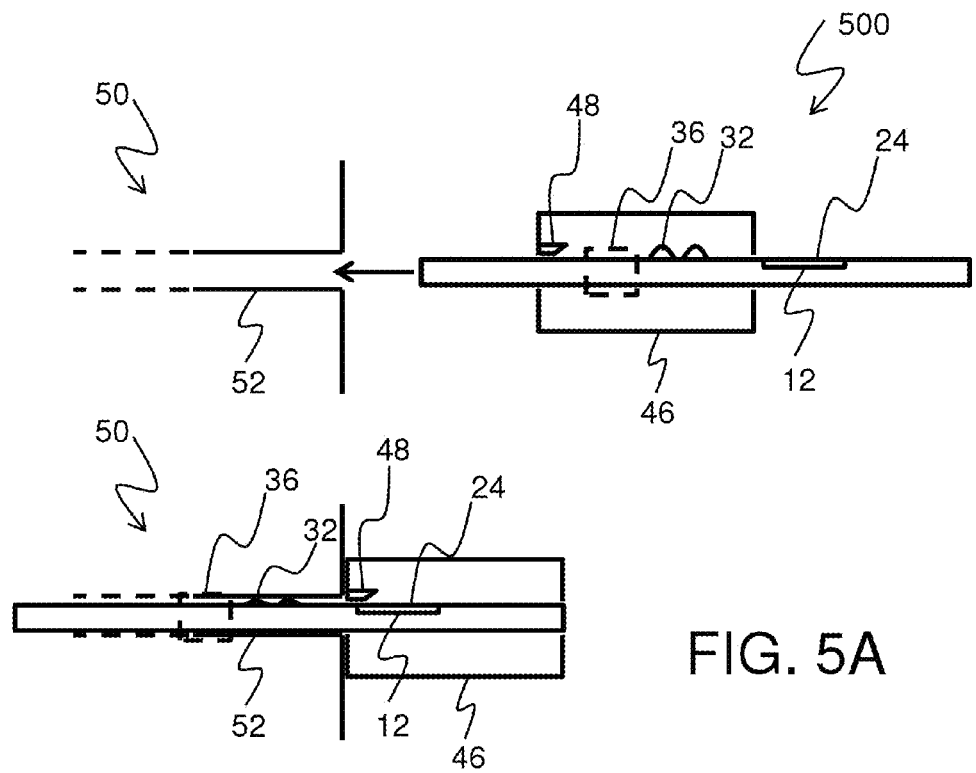
FIG. 5A shows a cross section of a microcuvette cartridge with a housing in external and inserted positions according to an embodiment of the present invention.
Figure 5B:
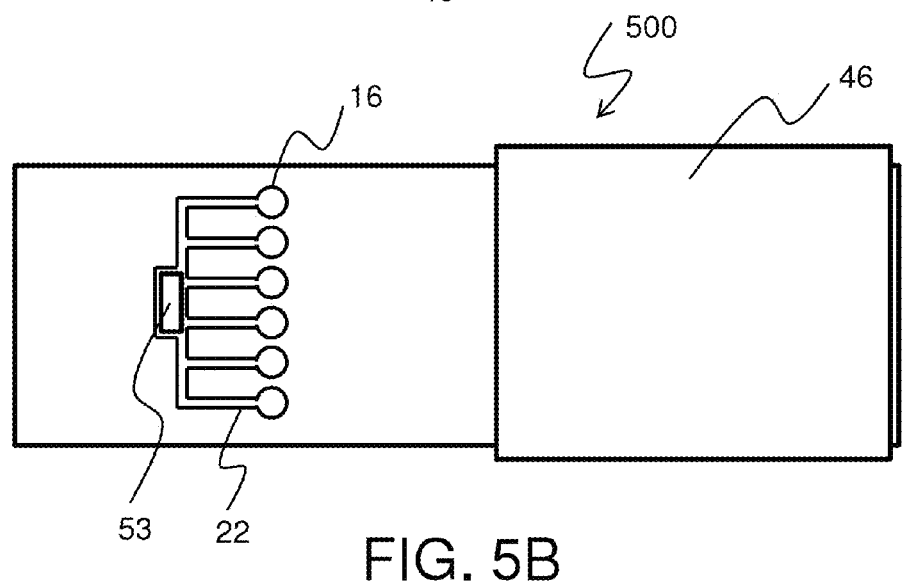
FIG. 5B is a bottom view of a microcuvette cartridge with a housing according to the embodiment of the present invention.

FIGS. 5A and 5B show another embodiment of the present invention. FIG. 5A shows a cross section of a microcuvette cartridge 500 in external and inserted positions according to the present embodiment. A housing 46 is provided to movably house the microcuvette cartridge 500 of the type shown in FIG. 3. The housing 46 has a pushing member 48. When the microcuvette cartridge 500 is inserted into a slot 52 of an optical measurement device 50, the housing 46 is pushed by the external wall of the optical measurement device 50 relative to the rest of the microcuvette cartridge 500. As a result, the pushing member 48 slides and squeezes the blister packs 28 and/or 32, which causes the liquid to discharge from the blister packs 28 and/or 32 and flow into the channels.

FIG. 5B is a bottom view of this embodiment. In this embodiment, the back channels 22 are consolidated at one location where an opening to the exterior is provided through a membrane 53. In this embodiment, the membrane 53 is configured to let only gas through and keep liquid inside by having an appropriate porosity and hydrophobicity, or permeability. The air or gas in the channels is pushed by the liquid from the blister packs 28 and/or 32 and is discharged through the membrane 53, which is disposed on the rear side of the cartridge 500. Accordingly, the cartridge of this embodiment can avoid bubbles in the channels and the microcuvettes. Further, in this embodiment, the housing 46 can be configured to protect the detection region 36 from dust or fingerprints.

As described above, capillary force can be used to cause the fluid to flow in the channels when both ends of the flow channels are open, and blister packs can be utilized to cause or assist the flow of the fluid in the channels. In the alternative, or in addition, vacuum techniques can be used to generate the flow. For example, PDMS can be used as a channel composition material. Under a vacuum, either at the time of manufacture or at the time of use, the channels made with PDMS shrink because of the flexibility of PDMS, and the channels may retain a vacuum or until a fluid is introduced. When the vacuum around the channels is broken, the channels suck the fluid positioned at its entrance. To use this method, part or entire of the cartridge can be packed in a vacuum foil (gas impermeable foil). For example, when the vacuum foil is opened and the vacuum is broken, the channels begin to suck the fluid and chemical agent, and then, several minutes later, all channels and microcuvettes can be filled with fluid and are ready for optical measurement. In the alternative, or in addition, a chemical reaction can be used to generate gas, and the gas can push the fluid and start the flow.

Also, a piezoelectric transducer, an ultrasonic transducer, and shaking the device by hand can cause the cartridge to vibrate, which can actuate and assist flow in the channel.

Figure 6:
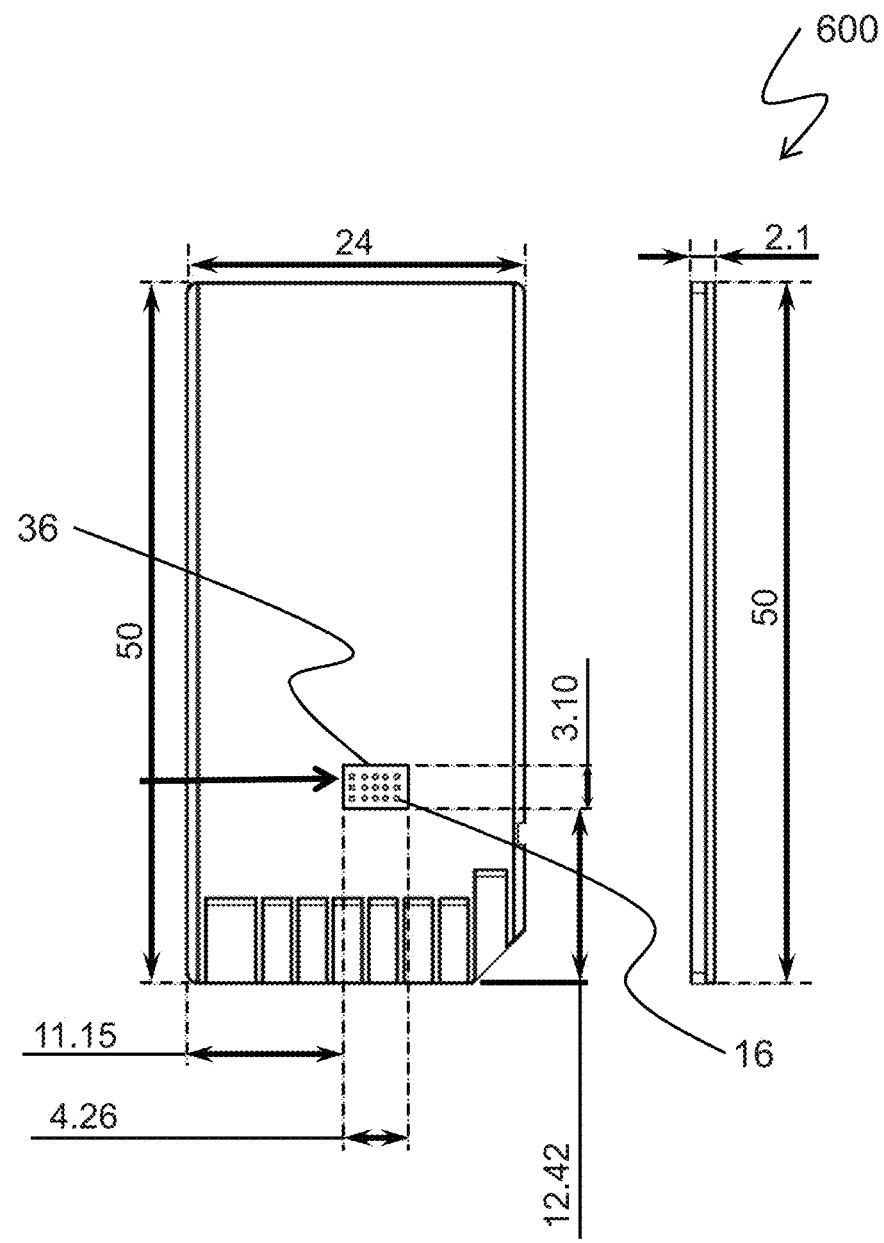
FIG. 6 shows an example of the dimensions of a microcuvette cartridge according to an embodiment of the present invention.

FIG. 6 shows an example of form factors any of the embodiments of the present invention can take. This exemplary microcuvette cartridge 600 has a form factor according to the SD card specifications. The units in the FIG. 6 are millimeters. In FIG. 6, the length of the cartridge is 50 mm, but this and other dimensions can be changed as necessary. The microcuvettes 16 are optically clear (365-800 nm), and the surrounding material may be opaque. Since the SD card specifications is one of the industry standards, a slot for an SD card, stabilization techniques, alignment techniques, and other common techniques can be used to design an optical measurement device that receive the microcuvette cartridge 600. Further, the microcuvette cartridge 600 of the present embodiment may have a plurality of terminals that allow electrical contact to external devices in accordance with the SD card specifications, and may be equipped with electrical circuits, chips, or memories so that the cartridge 600 can communicate with the host measurement device and store results of the measurement, and may also store additional data such as clinician, patient time and date, or provide information about the cartridge 600, such as batch lot, cartridge type or expiry date. With this feature, the user can check the results using a computer by inserting the SD card into the SD slot of the computer. Other usages of the terminals include, but are not limited to, short-circuiting a designated pair of the terminals by wiring in the cartridge 600 so that the host device can electrically recognize the insertion of the cartridge 600 by detecting electrical conduction between the pair of the terminals, installing a user selectable switch in the cartridge 600 for selectively short-circuiting plural pairs of the terminals for dip-switch like use, etc. Furthermore, microcuvette cartridges of the present invention may take other form factors that are widely recognized in various industries, such as form factors consistent with other memory card specifications, SIMS card specifications, or any other later developed standardized form factors that are convenient to users and for analysis may be adopted in the present invention.

Figure 7:
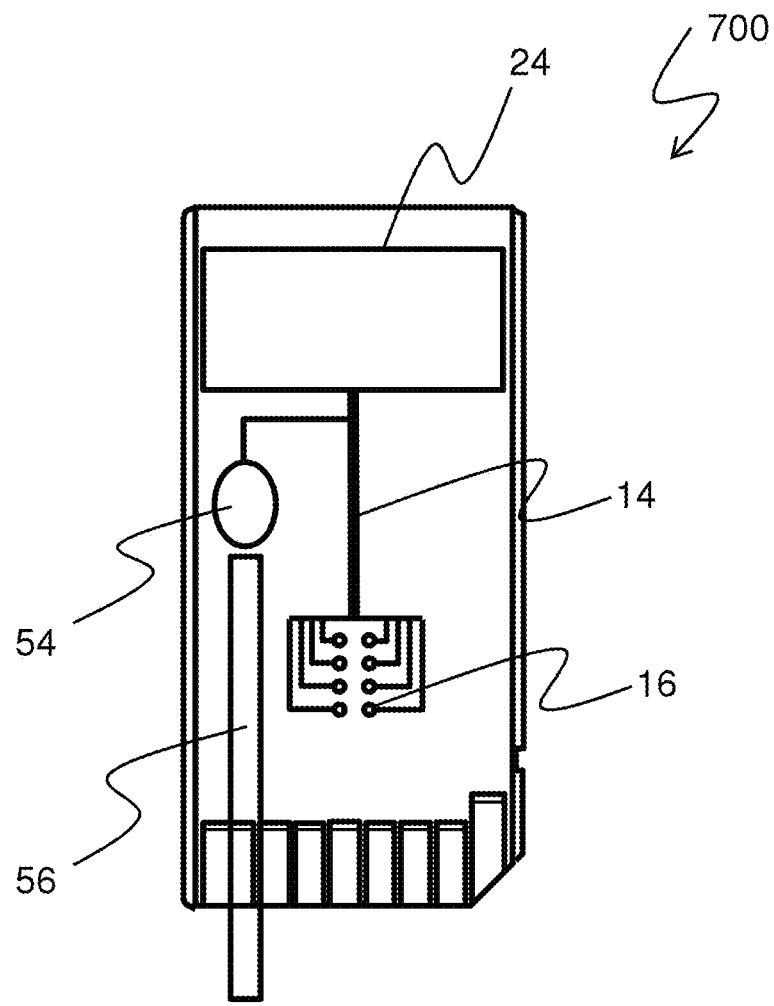
FIG. 7 is a schematic view of a microcuvette cartridge according to an embodiment of the present invention.

FIG. 7 schematically shows another embodiment of the present invention. The microcuvette cartridge 700 shown in FIG. 7 is based on the microcuvette cartridge 600 shown in FIG. 6, and additionally has a blister pack 54 and a pushing member 56. When the cartridge 700 is pushed into the slot of the optical measurement device, the pushing member 56 pushes the blister pack 54 to discharge the liquid contained in the blister pack 54 and actuate the flow of the fluid through the channels 14 to the microcuvettes 16.

Figure 8:
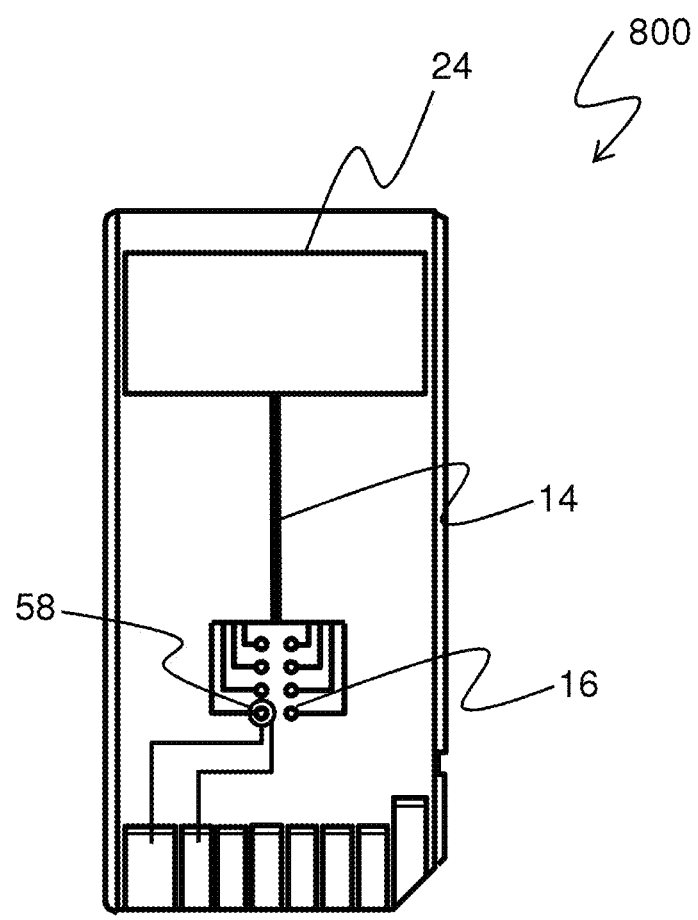
FIG. 8 is a schematic view of a microcuvette cartridge with a heating element according to an embodiment of the present invention.

FIG. 8 is a schematic view of another embodiment of the present invention and shows a microcuvette cartridge 800. The SD card format microcuvette cartridge 800 is based on the microcuvette cartridge 600 shown in FIG. 6, and additionally has heating elements 58. The heating elements 58 may be disposed only around one or more of the microcuvettes 16 to control the temperature in the vicinity of the microcuvettes 16, or may be installed throughout substantially the entire area of the cartridge 800 to control the temperature of the entire cartridge. The heating elements may be resistor-type heating elements energized by power provided through the terminals. Also, one or more temperature sensors may be disposed in the cartridge 800 to monitor the temperature. The temperature sensor may be a thermocouple with patterned electrodes connected to the terminals.

Figure 9:
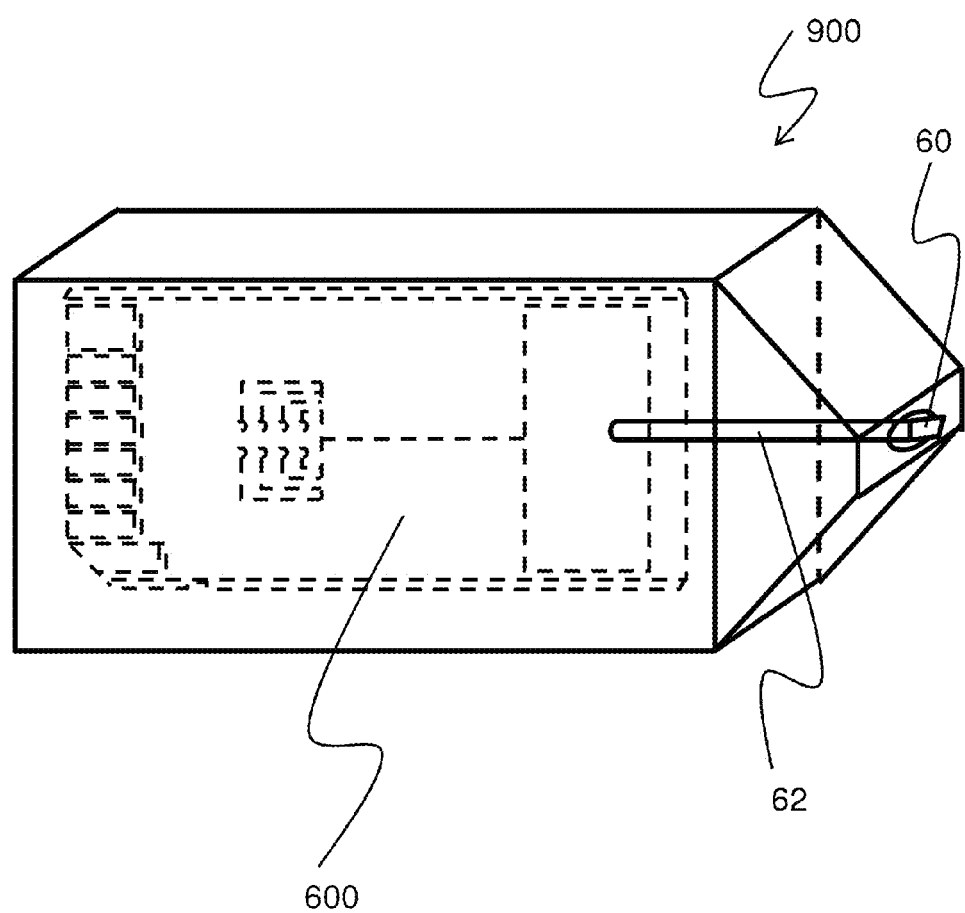
FIG. 9 is a schematic view of a microcuvette cartridge with a housing having an integrated lancet according to an embodiment of the present invention.

FIG. 9 shows another embodiment of the present invention. FIG. 9 is a schematic view of a lancet integrated package 900 according to the present embodiment. The lancet integrated package 900 has a lancet 60 and a pipe 62 connecting the lancet 60 to the blood collecting filter paper of the microcuvette cartridge 600 of FIG. 6, which is removably installed in the package 900. Using the lancet 60, a small amount of the required blood can be collected. The blood travels through the pipe 62 and is delivered to the filter paper and finally reaches to the microcuvettes in the microcuvette cartridge 600. The pipe 62 may be a capillary tube.

Figure 10A:
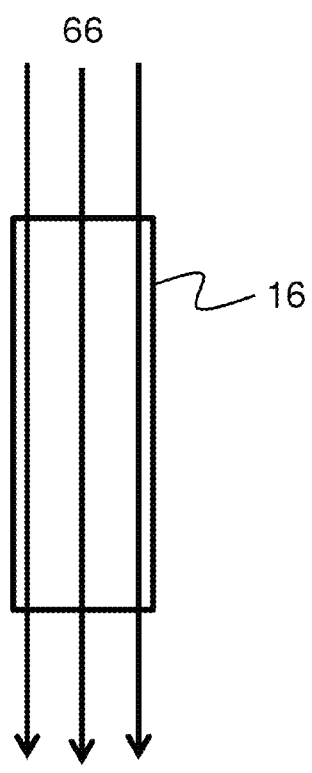
FIG. 10A shows an optical path for one of the microcuvettes in a microcuvette cartridge according to an embodiment of the present invention.
Figure 10B:
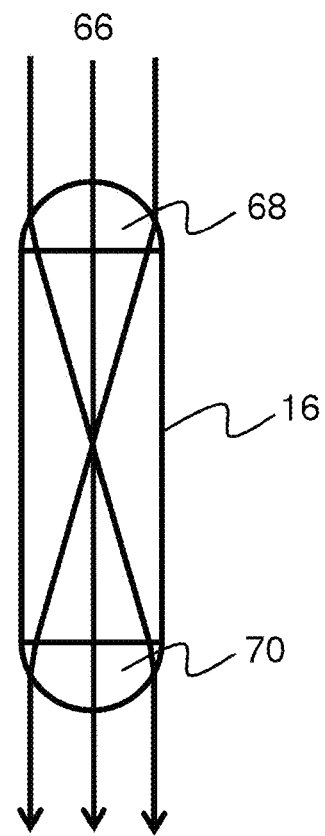
FIG. 10B shows an optical path for one of the microcuvettes in a microcuvette cartridge according to an embodiment of the present invention.

FIGS. 10A and 10B schematically show exemplary structures of an individual microcuvette 16 that can be used in any of the embodiments of the present invention. As shown in FIG. 10A, the microcuvette 16 may be configured to have a flat top surface and a bottom surface in parallel with each other. In this case, collimated light rays 66 generated by the host optical measurement device pass through the microcuvette 16 without substantial refraction. For certain optical measurement, this configuration may be desirable. FIG. 10B shows another example according to an embodiment of the present invention in which the microcuvette 16 has an upper convex lens 68 and a lower convex lens 70. The lenses 68 and 70 can be made by injection molding or other available techniques. When the collimated light 66 passes through the upper lens 68, the light is focused at the middle of the microcuvette 16. The light 66 is recollimated by the lower lens 70. By focusing the light in the cuvette in this way, the light rays that would pass near the inner vertical walls of the microcuvette without the lenses 68 and 70 will pass near the center of the microcuvette so that the influence of scattering at the inner vertical walls of the microcuvette can be mitigated. Also, because the energy density of the focused light is high at the focal point, strong interaction between the light and the fluid can occur there and can result in significant changes in the transmitted light, thereby increasing the signal to noise ratio. Furthermore, with the structure of FIG. 10B, the integrated microcuvette 16 can produce more consistent results regardless of density distribution of the analyte inside the microcuvette.

Figure 11:
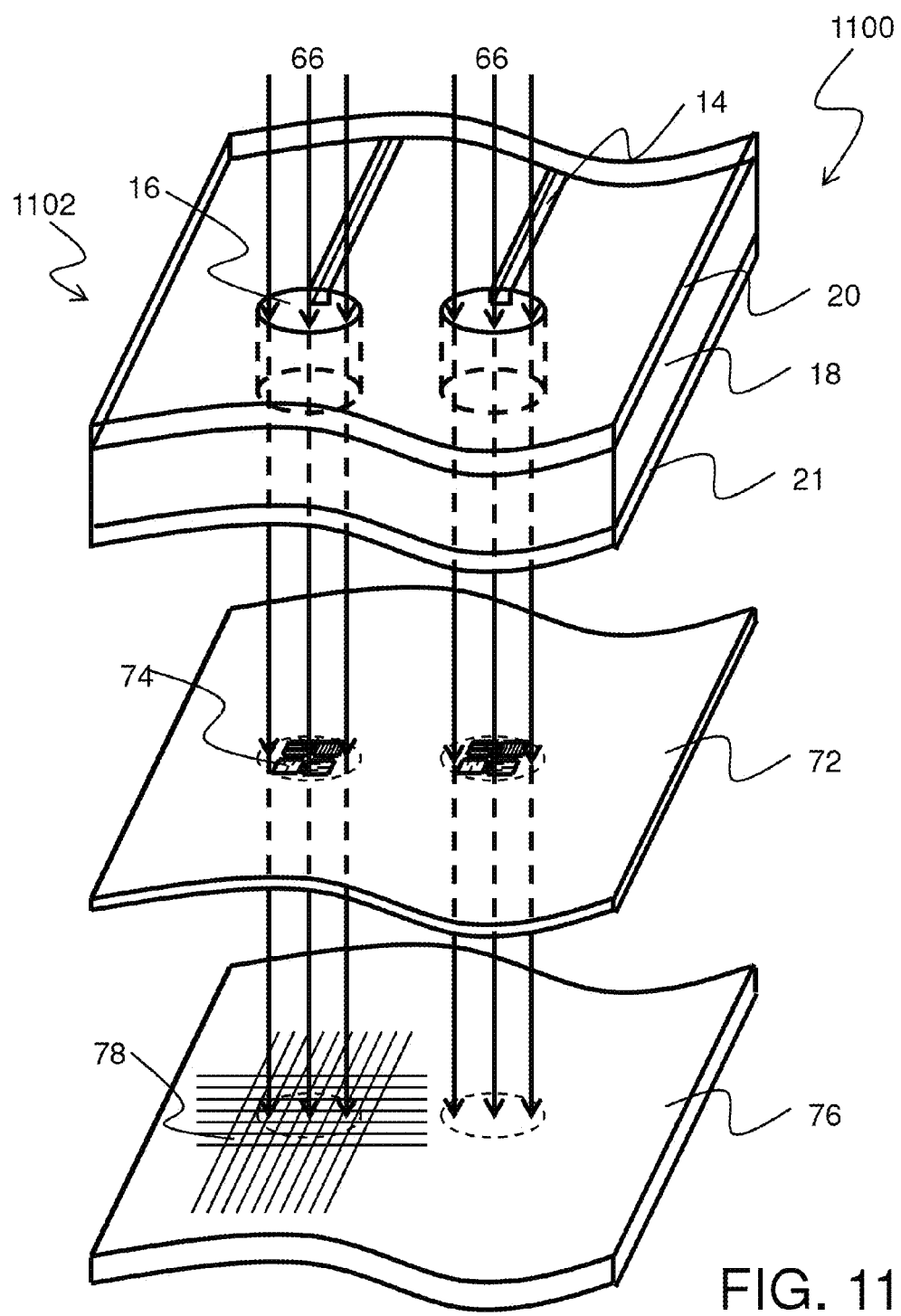
FIG. 11 schematically shows a configuration for optical examination of the specimen with the microcuvettes of a microcuvette cartridge according to an embodiment of the present invention.

FIG. 11 is a schematic view of an exemplary configuration 1100 for optical measurement using a microcuvette cartridge of an embodiment of the present invention. FIG. 11 shows a part of the microcuvette cartridge 1102. In this example, in order to conduct optical analysis of the specimen in the microcuvettes 16 (two shown in the figure), a color filter layer 72 and sensor 76 are disposed below the microcuvette cartridge 1102. Light 66 having an appropriate wavelength bandwidth is emitted from a light source from above the microcuvette cartridge 1102 as shown in FIG. 11. The light 66 then passes through the microcuvettes 16, and interacts with the analyte in the microcuvette 16, causing the light 66 to change its spectrum, for example. The light 66, which has passed through the microcuvettes 16, then reaches the color filter layer 72. The color filter layer 72 includes color filters 74 in the irradiated area. The color filter may be a structural color filter utilizing surface plasmon resonance, for example. Each color filter 74 selectively eliminates, enhances, or otherwise modifies the wavelength or intensity of selected light wavelengths during transmission. The filtered light 66 can be detected by one or more addressed pixels 78 in the sensor 76. Such measured changes in light intensity/spectrum can be used to monitor the presence, absence, or absolute or relative concentration of the analyte, or a change in concentration due to diffusion, flow, temperature, or kinetics of a reaction of the analyte diffusing into, held, bound in, or associated with the microcuvette 16. The host optical measurement device can be configured to have this or a similar arrangement of optics and parts within the device so that when it receive the microcuvette cartridge 1102 of the present invention in its insertion slot, the light rays 66, the color filter layer 72, and the sensor 76 are positioned appropriately relative to the microcuvette cartridge 1102 in a manner shown in FIG. 11.

Using a host optical measurement device of the type described above, a microcuvette cartridge according to an embodiment of the present invention may provide comprehensive metabolic panel (CMP) assays in a short time and in a manner convenient to the users. For example, some or all of the tests for CMP and/or lipid panel, such as tests for alanine transaminase, albumin, aspartate transaminase, calcium, chloride, creatinine, glucose, total bilirubin, carbon dioxide, total protein, blood urea nitrogen, alkaline phosphatase, potassium, sodium, triglycerides, cholesterol, and HDL can be conducted using a single microcuvette cartridge requiring only a small amount of blood. To this end, the microcuvette cartridge according to the present invention may be configured to include a number of microcuvettes that corresponds to the number of the tests to be conducted and an appropriate number of blister packs for discharging diluent and/or reagents or other chemicals appropriate for the respective tests.

Figure 12A:
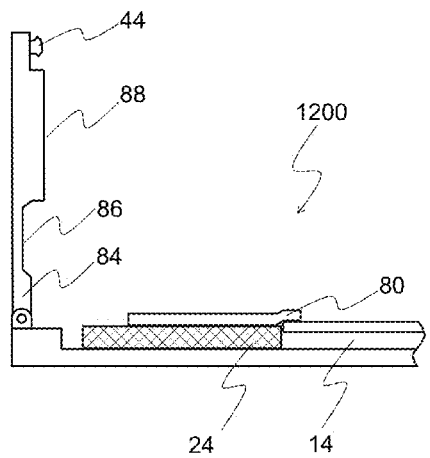
FIGS. 12A to 12D illustrate a fluid transport scheme of a microcuvette cartridge with a lid according to an embodiment of the present invention.
Figure 12B:
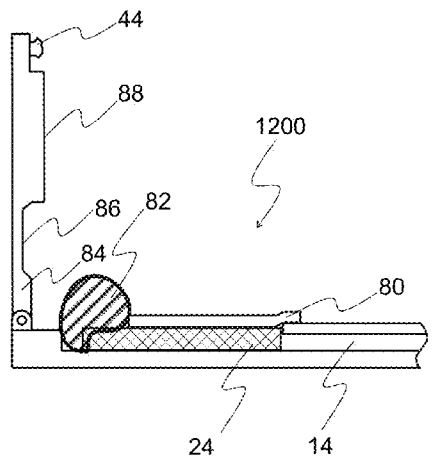
Figure 12C:
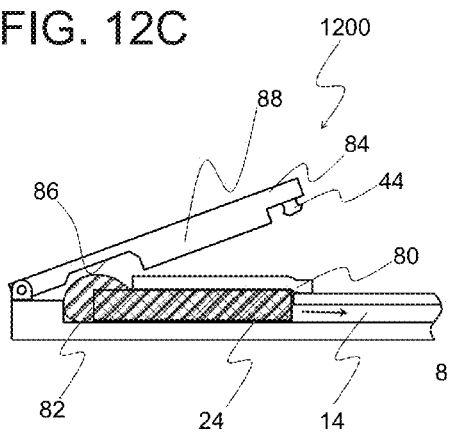
Figure 12D:
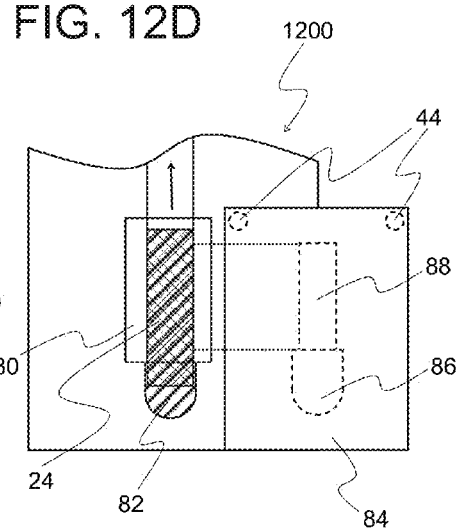

FIGS. 12A to 12D show another embodiment of the present invention. FIGS. 12A to 12C show cross sections and FIG. 12D shows a top view of a microcuvette cartridge 1200 adjacent to the sample receiving portion, showing an example of transport mechanism. In this embodiment, a filter paper 24 is partially (FIG. 12A) or completely covered with a cover sheet 80 made of a flexible material, such as a flexible polymer or hydrophilic adhesive tape. When blood 82 is introduced, as shown in FIG. 12B, the blood is absorbed into the filter paper 24, and the filter paper 24 expands or swells as a result. This passive action is completed fairly quickly. Afterwards, as shown in FIGS. 12C and 12D, a lid 84 having an enclosure 86, a bump 88, and a snap 44 is manually placed on an intermediate substrate with the hinge action (FIG. 12D shows the lid 84 is removed and placed on the right side to show the structure underneath). This results in three actions, and not necessarily at the same time. The enclosure 86 contains the blood 82 within the cartridge 1200. The snap 44 positions the lid in place. The bump 88 presses on the cover sheet 80 that is resting on the filter paper 24, which causes the filter paper 24 to release plasma into a channel 14. Filter paper 24 is appropriately designed so that only plasma is introduced into the channel 14 and red blood cells, etc., are prevented from entering the channel 14.

FIGS. 13A to 13C show another embodiment of the present invention. FIGS. 13A to 13C show cross sections of a filter paper region of a microcuvette cartridge 1300 and a blood dropper 1302, illustrating another example of transport mechanism. In this embodiment, the blood dropper 1302 is constructed of a bulb 90 and a tube 92 to collect a small amount of the specimen such as blood. For example, a user pricks finger, wipes first blood droplet, and operates blood dropper 1302 to draw blood. The blood will be metered inside the tube 92. As shown in FIG. 13A, the user places the tube 92 at the inlet port 94 of the cartridge 1300. The inlet port 94 may be formed in the cartridge through the top layer. The inlet port 94 is configured to provide a good seal for the tube 92 and the cartridge 1302. As shown in FIG. 13B, when the user squeezes the bulb 90 of the blood dropper 1302, the blood enters the filter paper 24 and plasma is released downstream into a channel 14. As shown in FIG. 13C, the inlet port 94 may be formed at the side of the cartridge 1300.

Figure 14A:
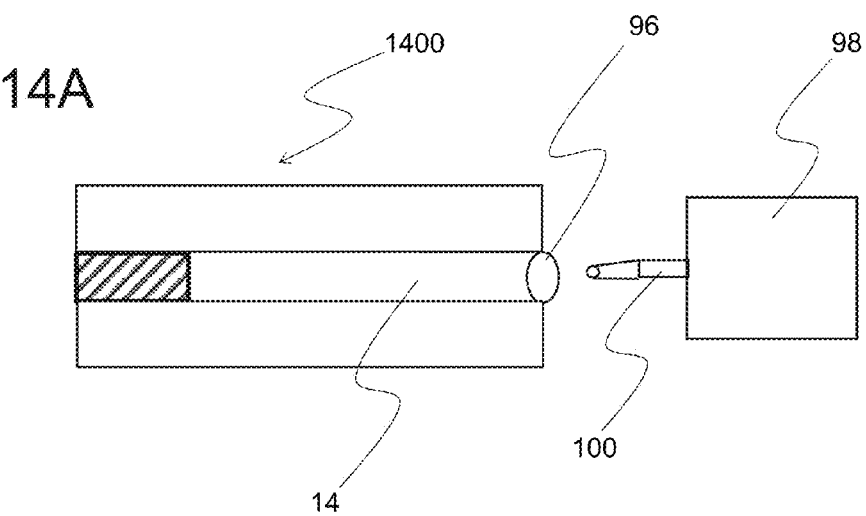
FIGS. 14A and 14B illustrate a fluid transport scheme of a microcuvette cartridge with a vacuum pump in external and inserted positions according to an embodiment of the present invention.
Figure 14B:
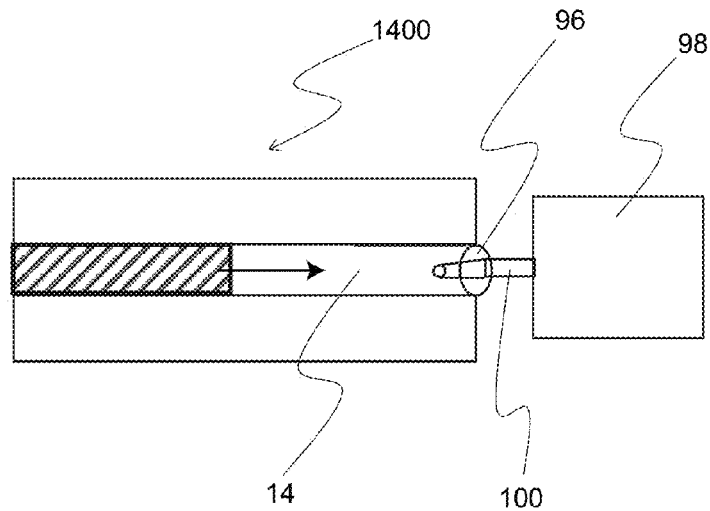

FIGS. 14A and 14B show another embodiment of the present invention. FIGS. 14A and 14B show a cross section of a part of a microcuvette cartridge 1400 and its arrangement with respect to a vacuum pomp 98 housed by a host device to which the cartridge 1400 is to be inserted. In this embodiment, a gasket 96 is configured at an outlet of the microcuvette cartridge 1400 and a vacuum pump 98 with a tubing 100 is placed in an optical measurement device (host device) that is designed to receive the cartridge 1400. To actuate biological fluid, reagents, and diluent in the microcuvette cartridge 1400, a pneumatic system can be connected to a cartridge, once the cartridge is introduced into the optical measurement device. As shown in FIG. 14A, the cartridge outlet contains the gasket 96. As shown in FIG. 14B, when the microcuvette cartridge 1400 is slid into an insertion slot of the optical measurement device, the gasket 96 fits into the tubing 100 to form a seal for the vacuum to withdraw air/liquid in the channel 14. A similar setup can be achieved for a positive pressure pneumatic pump. Sealing of the channel enables optimized fluid actuation. Air or liquid along with reagents, diluent, and buffers are medium that can be actuated from this setup.

FIGS. 15A to 15C show another embodiment of the present invention. FIGS. 15A to 15C show cross sections of a portion of a microcuvette cartridge having a blister pack 102. This embodiment is a multistep fluid transfer scheme. The example shown in the figures is two-step compressing mechanism. In this embodiment, as shown in FIG. 15A, walls 104 are formed at two opposing sides or all the sides of the blister pack 102. To discharge the content of the blister pack 102, a compressing member 106 is placed over the blister pack 96. FIGS. 15B and 15C show a two-step release scheme; first, the compressing member 106 is lowered only half-way to compress the blister pack 102 half-way to release a portion of the fluid to the a channel 14 through the fluid exit passage 116, and second, the compressing member 106 is lowered further down to fully compress the blister pack 102 such that most of the fluid exits the blister pack 102 through the fluid exit passage 116 into the channel 14. Compressing actions from the side can have the same effect. Further, depending on the structure and material of the blister pack, the walls 104 may not be necessary.

Cartridges for diagnostic applications have a limited surface area. Blister packs storing reagents and/or diluents and an actuating fluid may occupy a large area (more than 15% of the entire area) of the cartridge surface. Oftentimes, multiple packs are used for the same liquid to deliver liquid into the cartridge. According to this embodiment, since the blister pack 102 is compressed in two steps, fluid in the blister pack 102 is released into the channel 14 in two phases. Thus, the fluid in the blister pack 102 can be controllably released, and as a result, the number of the required blister packs 102 for the microcuvette cartridge can be reduced, making a further reduction of the cartridge size possible.

FIGS. 16A-16C shows another embodiment of the present invention. This example is a self-powered integrated microfluidic cartridge 1600 for blood-based diagnostic assay. The microcuvette cartridge 1600 has a blood port 108 for receiving a small amount of blood, a filter paper 24 for filtering blood, a plurality of first flow restrictor 110, a plurality of blister packs or inlets of reagents 112, a plurality of second flow restrictors 114, channels 14 (8 channels are show in the drawing), mixing channels 34, and a plurality of microcuvettes 16. A detection region 36 is defined as a region where the array of the microcuvettes 16 is disposed. In this embodiment, as shown in FIG. 16B, which is a cutaway view of the vicinity of one channel 14, the channels 14 are formed in a PDMS fluidic layer 131 (100 micron), and the channels 14 are sealed by a glass layer 132 on bottom and a PMMA-PS layer 133 on top. Other appropriate materials mentioned above can also be used for these layers. In particular, the PDMS layer 131 of the present embodiment can be replaced with other porous polymers or like materials for degassing and driving purposes, which will be described in detail below. The entire structure of the cartridge 1600 may be constructed by the three-layered structure depicted in FIG. 16B. To avoid the PDMS middle layer from contacting the outside environment, any surfaces of the PDMS middle layer that are exposed to the exterior, if any, are coated with a non-air-permeable layer or material. The channel 14 or other structures of the cartridge 1600 may alternatively be formed by bottomed grooves on the top or bottom surface of the middle layer 131 sealed by the corresponding top or bottom layers 133, 132, as in the embodiments described above. After blood is placed on the blood port 108, plasma is separated from whole blood with the filter paper 24 (about 10% to about 20% of the blood is filtered out), and the resulting fluid (plasma) is wicked into the PDMS fluidic channels 14.

In this embodiment, degassing of the channels 14 and driving of the fluid specimen (separated plasma in this embodiment) into the channels 14 towards the microcuvettes 16 are performed by the following scheme. First the cartridge is placed in a vacuum or any appropriate low pressure environment, and is packaged and sealed. A commercial product of this embodiment may be such a vacuum packaged cartridge. When a user breaks the package and exposes it to the air under the atmospheric pressure, voids such as channels 14 and cavities 16 in the cartridge 1600 are almost immediately filled with the air of the atmospheric pressure. On the other hand, the pressure inside the PDMS fluidic channels gradually rises. This creates relatively gradual and continuous suction force by the sidewalls of the channels 14 (and cavities 16, if their sidewalls are also at least partially formed by PDMS) so as to drive the fluid specimen downstream. In other words, this degassing mechanism takes advantage of the PDMS polymer (or like material) that, when removed out of vacuum, becomes a sponge for air molecules to restore into equilibrium. This restoration drives fluid downstream. The degassing mechanism may also be provided for the filter paper 24. For example, sidewalls or surfaces of the PDMS polymer may be placed in the vicinity of the filter paper 24 so that wicking of plasma downstream is promoted by the suction force.

The fluid specimen that has been driven by the suction force as described above first reaches a set of the first flow restrictors 110. The first and second flow restrictors 114 are strategically placed in some or all of the channels 14 to regulate the flows of the fluids in the respective channels 14. Although only a few flow restrictors are shown in FIG. 16A, in this embodiment, all the channels 14 are equipped with the first and second flow restrictors 110 and 114. In this embodiment, as shown in FIG. 16C, the flow restrictors 110, 114 are formed in the form of a pinched portion in the channel 14. Any of the first and second flow restrictors 110 and 114 may also be formed by making the inner faces of a portion of the channel 14 hydrophobic in addition to or in the alternative to the pinched channel structure shown in FIG. 16C. These flow restrictors can serve to stop the fluid flow in all channels and enable filling of plasma of all channels (metering) at the equal or substantially equal timing. In this embodiment, these flow restrictors are designed to completely stop the flow of the fluid in the channel until a certain pressure differential is developed between the inlet and the outlet of the flow restrictor. Once the plasma reaches the first flow restrictors 110, the plasma in the respective channels is stopped until the sidewalls of the PDMS layer further removes the air in the channels and develops additional pressure differential. Once a sufficient pressure differential is developed, the plasma starts re-flowing downstream again, and then reaches a set of the second flow restrictors 114. Similar to the first flow restrictors, the stepped plasma/fluid specimen is released and starts moving downstream at substantially the same time once a larger pressure differential is developed due to the suction of the air by the PDMS layer downstream.

In this embodiment, while the plasma flows are stopped at the second flow restrictors 114, reagents deposited in the channel (which can be accomplished through inlet ports 112 for reagent deposition or blister packs containing reagents placed in the locations of these ports as described above) prior to the flow restrictors 114 can react with the stationary plasma, causing a stable reaction to occur, thereby producing a fluid specimen with the desired characteristics for analysis. Thus, the flow restrictors 114 can act as temporary stop points for the plasma and enable the sample to react with the reagent to form a desired fluid specimen. The timing of the fluid flow can be synchronized by appropriately designing the dimensions and length of each channel and the properties and locations of the flow restrictors 110, 114 such that the fluid specimen can be moved downstream to the microcuvettes 16, respectively, at substantially the same time.

As described above, like other embodiments described above, blood plasma may be diluted with a diluent before metering. A blister pack 118 (FIG. 16A) may be optionally installed to contain and release the diluent before metering the plasma, and various mixing schemes can be utilized to effectively mix the blood plasma with the diluent. The mixing may be accomplished by 3D channels or a set of pillars in expanded chambers, for example. Plasma metering can be achieved through flow restrictors 110/114 or contraction channels or a small hydrophobic region with low surface energy. Once the blister pack 118 is actuated, the diluent pushes the plasma through the flow restrictors 110 into the mixing region. The blister pack can be actuated by various ways, as described above. For example, as described with reference to FIG. 5 above, the cartridge can be inserted into a housing 46 that pushes down the blister pack 118.

If the embodiment with the blister pack 118 is further equipped with the lit structure 84 shown in FIGS. 12A-12D, the timing of the blister pack actuation is not important because once the user closes the lid 84 of the microcuvette cartridge 1600, the bump 88 pushes on the filter paper that releases the plasma into compartmentalized channels for metering. At this point, the plasma stays stagnant in these channels unless further actuated with the blister pack 118. When the user inserts the cartridge into the housing 46 with lid closed (FIG. 5), the blister packs are ready to be actuated. An appropriately designed pushing member(s) or jig(s) may be installed within the housing 46 to actuate all of the blister packs simultaneously if a plurality of blister packs are installed in the cartridge and if such simultaneous actuation of the blister packs are desired. Alternatively, the blister pack 118 can be actuated manually.

The present invention is not limited to microscale cuvettes for spectroscopy. Applications to other optical or electrical measurement schemes are also contemplated. For dimensions and size, each of the microcuvettes described above may be larger than 1 mm in any dimensions. As long as the portability of the cartridge is preserved, there is no specific limitation in the dimensions of the cuvettes 14 or other structures and elements of the cartridge. Furthermore, particular dimensions and the amounts of the fluids, specimens, reagents, diluents, etc., mentioned above are merely exemplary. Furthermore, embodiments of the present invention can be made to be disposable. Such disposable cartridges enables automated sample preparation in small sample volumes and can be aligned with a reader or an appropriate host device, which reads or analyzes the fluid specimen as it flows or is stationary in the cartridge reading channel. The system can be designed such that the reading instrument/the host device is not exposed to the biological fluid, material, or reagents associated with the cartridge.

It will be apparent to those skilled in the art that various modification and variations can be made in the present invention without departing from the spirit or scope of the invention. Thus, it is intended that the present invention cover modifications and variations that come within the scope of the claims that eventually issue in a patent(s) originating from this application and their equivalents. In particular, it is explicitly contemplated that any part or whole of any two or more of the embodiments and their modifications described above can be combined and regarded as part of the present invention.

What is claimed is:

1. A microcuvette cartridge configured to be inserted into an opening of a receiving apparatus in a first direction, comprising:

a substrate having a recess on an upper surface thereof to receive a fluid specimen therein, said substrate having a plurality of cavities therein to receive the fluid specimen transported from the recess, said substrate further defining a plurality of channels communicating with the recess and with the plurality of cavities, respectively, to transport the fluid specimen from the recess to the plurality of cavities, said substrate further having one or more of windows at positions corresponding to the plurality of cavities, the windows being transparent to prescribed wavelengths of light so as to allow the light to interact with the fluid specimen in the cavities for the optical measurement, the substrate having a front end to be inserted into the opening of the receiving apparatus and a rear end that is opposite to the front end, said one or more of windows and said recess being arranged in the first direction with said one or more of windows disposed closer to said front end than said recess; and a transport mechanism to promote and complete flows of the fluid specimen from the recess to the plurality of cavities through the plurality of channel, wherein the transport mechanism comprises;

an air-discharge membrane that can pass air therethrough and that blocks the fluid specimen, wherein said substrate further includes discharge channels communicating with the plurality of cavities and reaching the air-discharge membrane;

one or more of blister packs containing a liquid solution therein, connected to one or more of the plurality of channels, the blister pack being configured to discharge the liquid solution into the corresponding channel when pressed and deformed with external force; and a flow blocking membrane disposed adjacent an outlet of the recess connected to the plurality of channels so as to substantially prevent a reverse flow of the fluid specimen, wherein when the blister pack is pressed, the liquid solution is discharged to the corresponding channel, wherein the microcuvette cartridge further comprises a housing that laterally movably houses at least a portion of the substrate with said transport mechanism, said housing being movable relative to said at least the portion of the substrate in the first direction that is parallel to the upper surface of the substrate, said housing including a pushing member fixed to the housing such that when said substrate is laterally pushed relative to the housing in the first direction, the pushing member laterally engages with the blister pack in the first direction to cause the blister pack to discharge the liquid solution into the channel, and wherein when the cartridge is not inserted into the opening of the receiving apparatus, the housing is positioned so as to cover said one or more windows, and the housing has such dimensions that when the cartridge is inserted into the opening of the receiving apparatus, the housing is pushed back by the receiving apparatus towards the rear end of substrate so as to expose said one or more windows inside the receiving apparatus and so that the pushing member laterally engages with the blister pack as a result of the insertion.

2. The microcuvette cartridge according to claim 1, wherein the blister packs contain one or more of reagents to be mixed with the fluid specimen.

3. The microcuvette cartridge according to claim 1, wherein said substrate comprises an upper plate, an intermediate substrate, and a lower plate.

4. The microcuvette cartridge according to claim 1, wherein dimensions of said substrate are dimensions of a SD card.

5. The microcuvette cartridge according to claim 1, wherein said substrate comprises a bottom layer, a top layer, and an intermediate substrate interposed between the bottom layer and the top layer, and wherein at least some of the plurality of channels are defined by a groove in a top surface of the intermediate substrate and the top layer formed thereon.

6. The microcuvette cartridge according to claim 1, wherein at least a portion of said substrate comprises a bottom layer, a top layer, and an intermediate layer interposed between the bottom layer and the top layer, and wherein the bottom layer is made of glass, the top layer is made of polymethyl methacrylate (PMMA)/polystyrene (PS), and the intermediate layer is made of polydimethylsiloxane (PDMS).

7. The microcuvette cartridge according to claim 1, wherein at least some of the plurality of channels have a flow restrictor to temporarily stop a flow of the fluid specimen in the channel.

* * * * *